United States Patent [19]

Nassim et al.

[11] Patent Number: 4,849,427

[45] Date of Patent: Jul. 18, 1989

[54] NEDOCROMIL CALCIUM AND USE THEREOF IN TREATMENT OF REVERSIBLE OBSTRUCTIVE AIRWAYS DISEASE

[75] Inventors: Michael A. Nassim, Old Dalby; Richard A. Raphael, Kingston-on-Soar, both of England

[73] Assignee: Fisons PLC, Ipswich, England

[21] Appl. No.: 159,841

[22] Filed: Feb. 24, 1988

[30] Foreign Application Priority Data

Feb. 28, 1987 [GB] United Kingdom ................. 8704773

[51] Int. Cl.$^4$ .................... A61K 31/435; C07D 491/00
[52] U.S. Cl. ......................................... 514/291; 546/92
[58] Field of Search ........................... 546/92; 514/291

[56] References Cited

FOREIGN PATENT DOCUMENTS 2022078 5/1977 United Kingdom .................. 546/92

Primary Examiner—Mary C. Lee
Assistant Examiner—Robert C. Whittenbaugh
Attorney, Agent, or Firm—Marshall, O'Toole, Gerstein, Murray & Bicknell

[57] ABSTRACT

There are described a new compound, methods for its preparation and compositions containing it.

Calcium 9-ethyl-6,9-dihydro-4,6-dioxo-10-propyl-4H-pyrano[3,2-g]-quinoline-2,8-dicarboxylate is a novel compound and is useful in the treatment of reversible obstructive airways disease and/or the prevention or treatment of rhinitis.

9 Claims, No Drawings

NEDOCROMIL CALCIUM AND USE THEREOF IN TREATMENT OF REVERSIBLE OBSTRUCTIVE AIRWAYS DISEASE

This invention relates to a new compound, methods for its preparation and compositions containing it.

Disodium 9-ethyl-6,9-dihydro-4,6-dioxo-10-propyl-4H-pyrano[3,2-g]-quinoline-2,8-dicarboxylate, commonly known as nedocromil sodium, is disclosed in British Patent Specification No. 2,022,078. Nedocromil sodium is useful inter alia in the treatment of reversible obstructive airways disease. However, whilst nedocromil sodium has considerable duration of action it is sometimes of insufficient duration of action to enable a patient to obtain a full night's sleep. Further, some patients experience side effects with nedocromil sodium, including a feeling of warmth or an undesirable taste.

Surprisingly, we have now found that calcium 9-ethyl6,9-dihydro-4,6-dioxo-10-propyl-4H-pyrano[3,2-g]-quinoline-2,8-dicarboxylate possesses advantageous properties.

According to the invention, we provide calcium 9-ethyl-6,9-dihydro-4,6-dioxo-10-propyl-4H-pyrano[3,2-g]-quinoline-2,8-dicarboxylate.

Calcium 9-ethyl-6,9-dihydro-4,6-dioxo-10-propyl-4H-pyrano[3,2-g]-quinoline-2,8-dicarboxylate is also referred to as nedocromil calcium.

We further provide a process for the manufacture of nedocromil calcium which comprises:

(a) reacting a solution of a suitable salt of 9-ethyl-6,9-dihydro-4,6-dioxo-10-propyl-4H-pyrano[3,2-g]-quinoline-2,8-dicarboxylic acid with an appropriate solution containing calcium cations in available form, or (b) reacting 9-ethyl-6,9-dihydro-4,6-dioxo-10-propyl-4H-pyrano[3,2-g]-quinoline-2,8-dicarboxylic acid or a suitable ester or amide thereof, with a base containing the calcium cation in available form.

In the reaction of process (a), the salt of 9-ethyl-6,9-dihydro-4,6-dioxo-10-propyl-4H-pyrano[3,2-g]-quinoline-2,8-dicarboxylic acid may be any water soluble salt, e.g. an alkali metal salt, such as the sodium salt. The salt used as starting material may, if desired, have been formed in situ, e.g. by hydrolysis of the corresponding ester, and need not be isolated before use in a metathetical process.

In the reaction of process (b), acceptable esters include esters with C 1 to 10 alcohols, e.g. alkyl C 1 to 6 esters and esters with benzyl alcohol. The amides may be, for example, unsubstituted or mono- or di- C 1 to 6 alkyl amides and may be made by conventional techniques, e.g. reaction of an ester of the corresponding acid with ammonia or an appropriate amine.

The reactions of processes (a) and (b) may be carried out in a solvent which is inert under the reaction conditions. The solvent is preferably one in which the calcium salt is relatively insoluble, e.g. acetone or water. The temperature of the reaction may be varied.

The calcium cations may be provided by any conventional form of calcium which has an appropriate solubility for dissolution in the solvent of choice, e.g. when the solvent is water, calcium nitrate.

Preparation of 9-ethyl-6,9-dihydro-4,6-dioxo-10-propyl-4H-pyrano-[3,2-g]-quinoline-2,8-dicarboxylic acid is discussed in British Patent Specification No. 2,022,078.

The nedocromil calcium may be isolated and purified, for example by filtration and/or crystallisation.

Nedocromil calcium may exist in various hydrated forms. Nedocromil calcium comprising from 12 to 25% w/w, preferably from 15 to 25% w/w and more preferably from 15 to 20% w/w of water is more easily dried to a form suitable for use in pharmaceutical formulations which require a low water content or is less hygroscopic than other forms of nedocromil calcium.

We prefer nedocromil calcium to be in a form which has a low solubility in water, preferably less than 5% w/v in water at room temperature, more preferably less than 3% w/v and especially less than 1.5% w/v.

We also provide nedocromil calcium according to the invention in admixture with a pharmaceutically acceptable adjuvant, diluent or carrier, the type of adjuvant, diluent or carrier varying depending upon the disorder being treated.

The compound according to the invention is advantageous in that it is more efficacious or more potent in certain pharmacological models, or is less rapidly absorbed, or is longer acting, or causes fewer undesirable side effects than other similar compounds, eg nedocromil sodium.

The compound of the invention is useful because it possesses pharmacological activity in animals; in particular, it is useful because it inhibits the release and/or action of pharmacological mediators which result from the in vivo combination of certain types of antibody and specific antigen, e.g. the combination of reaginic antibody with specific antigen (see Example 27 of British Patent Specification No. 1,292,601). The new compound has also been found to interfere with reflex pathways in experimental animals and man, and in particular those reflexes associated with lung function. In man, both subjective and objective changes which result from the inhalation of specific antigen by sensitised subjects are inhibited by prior administration of the new compound. Thus, the new compound is indicated for use in the treatment of reversible airway obstruction and/or to prevent the secretion of excess mucus. The new compound is thus indicated for the treatment of allergic asthma, so-called 'intrinsic' asthma (in which no sensitivity to extrinsic antigen can be demonstrated), bronchitis, coughs and the nasal and bronchial obstruction associated with the common cold. The new compound may also be of value in the treatment of other conditions in which antigen-antibody reactions or excess mucous secretion are responsible for, or an adjunct to, disease, for example, hay fever; alimentary allergy, e.g. urticaria and atopic eczema; and gastro-intestinal conditions, for example, gastro-intestinal allergy, especially in children, e.g. milk allergy, or ulcerative colitis;

conjunctivitis, keratitis, 'allergic eyes', adenovirus infections, corneal homograft rejection, anterior uveitis;

nasal polyps, vasomotor rhinitis, allergic manifestations of the nasopharynx;

reversible obstructive airways disease;

Crohn's disease, distal colitis and proctitis.

By the term 'conjunctivitis' we mean inflammatory disorders of the conjunctiva commonly characterised by photophobia and irritation. The condition may be bacterial or viral and encompasses a number of specific types of conjunctivitis; for instance, seasonal allergic conjunctivitis, perennial allergic conjunctivitis, vernal catarrh (vernal kerato-conjunctivitis), 'irritable eye' or 'non-specific conjunctivitis', Herpes Simplex Conjunctivitis, Herpes Zoster Conjunctivitis and phlyctenular conjunctivitis.

Similarly, by the term 'keratitis' we mean inflammation of the cornea which may involve its superficial surface ('superficial keratitis' including the localised form known as 'corneal ulceration') or be confined to the deeper layers ('interstitial keratitis'). Other particular forms of keratitis which may be mentioned include Herpes Simplex Keratitis and Herpes Zoster Keratitis.

Proctitis includes chronic (i.e. ulcerative) and non-specific proctitis.

For the above-mentioned uses, the dosage administered will, of course, vary with the mode of administration and the treatment desired. However, in general, satisfactory results are obtained when the compound is administered at a dosage of from 0.001 to 50 mg per kg of animal body weight in the test set out in Example 27 of British Patent Specification No. 1,292,601. For man, the indicated total daily dosage is in the range of from 0.01 to 1,000 mg, preferably from 0.01 to 600 mg, and more preferably from 1 to 200 mg, which may be administered in divided doses from 1 to 8 times a day or in sustained released form.

According to the invention we provide the use of nedocromil calcium in the manufacture of a medicament for the treatment of reversible obstructive airways disease and/or the prevention or treatment of rhinitis.

According to the invention we further provide a method of treatment of reversible obstructive airways disease and/or rhinitis, which comprises administering a therapeutically effective amount of nedocromil calcium to a patient suffering from such a condition.

The compound according to the invention may be administered orally, rectally or topically. By the term topically we include administration to the skin, by oral inhalation, intranasally or to the eye. We prefer the compound according to the invention to be administered by oral inhalation, or intranasally, or to the eye.

For administration by nasal inhalation, nedocromil calcium may be administered as a powder, a nasal spray in the form of a solution or a suspension, or as a combination, e.g. wherein a portion of the medicament is dissolved and the remainder of the medicament is in suspension. When the medicament is administered part in solution and part in suspension, this has the advantage that a primary dose may be administered accompanied by a maintenance dose. We prefer the compound to be administered as a pressurised aerosol and particularly in such a manner for deposition to occur in the posterior part of the nose. The medicament delivered by pressurised aerosol may be in the form of a solution or a suspension. The aerosol propellant may deliver a pressure of from 138 to 551 kPa, preferably from 207 to 483 kPa and most preferably 276 to 414 kPa.

According to the invention we further provide a pressurised aerosol formulation comprising nedocromil calcium in admixture with a liquefied propellant.

For administration as a pressurised aerosol, we prefer nedocromil calcium with a water content of less than 5% w/w, preferably less than 4% w/w, more preferably less than 3% w/w and especially less than 2.5% w/w.

The liquefied propellant medium, and indeed the total formulation is preferably such that the nedocromil calcium does not dissolve therein to any substantial extent.

The liquefied propellant is preferably a gas at room temperature (20° C.) and atmospheric pressure, i.e. it should have a boiling point below 20° C. at atmospheric pressure. The liquefied propellant should also be non-toxic. Among the suitable liquefied propellants which may be employed are dimethyl ether and alkanes containing up to five carbon atoms, e.g. butane or pentane, or a lower alkyl chloride, e.g. methyl, ethyl or propyl chlorides. The most suitable liquefied propellants are the fluorinated and fluorochlorinated lower alkanes such as are sold under the Registered Trade Mark 'Freon'. Mixtures of the above mentioned propellants may suitably be employed.

The composition may also contain a surface active agent. The surface active agent may be a liquid or solid non-ionic surface active agent or may be a solid anionic surface active agent.

The preferred solid anionic surface active agents are the docusate salts, e.g. calcium docusate or sodium docusate.

The amount of the surface active agent required may be related to the solids content of the suspension and to the particle size of the solids.

When a liquid, non-ionic surface-active agent is employed it may have an hydrophile-lipophile balance (HLB) ratio of less than 10. It is possible to employ mixtures of surface-active agents, the mixture having an HLB ratio within the prescribed range.

Those surface-active agents which are soluble or dispersible in the propellant are effective. The more propellant-soluble surface-active agents are the most effective.

Any conventional liquid non-ionic surface-active agents may be employed, eg the esters or partial esters of fatty acids containing from 6 to 22 carbon atoms.

We particularly prefer compositions containing a sorbitan or sorbitol ester, eg sorbitan trioleate, in a mixture of propellants.

We prefer packages containing from about 8 to 30 ml of composition, e.g. a conventional aerosol pressure pack of 10 ml. The pack preferably has a valve adapted to deliver unit dosages of between 0.025 and 0.25 ml, and preferably 0.05 or 0.1 ml, of composition. We prefer the valve to deliver 1 to 5 mg of nedocromil calcium per actuation, preferably 1 to 4 mg, more preferably 2 to 4 mg and especially 2.6 mg per actuation, and unit doses of these quantities of the drug are provided.

The compositions of the invention may be made by mixing the various components at a temperature and pressure at which the propellant is in the liquid phase and the nedocromil calcium is in the solid phase.

In producing the compositions and packages of the invention, a container equipped with a valve is filled with a propellant containing the finely-divided nedocromil calcium in suspension. A container may first be charged with a weighed amount of dry nedocromil calcium which has been ground to a predetermined particle size, or with a slurry of powder in the cooled liquid propellant. A container may also be filled by introducing powder and propellant by the normal cold filling method, or a slurry of the powder in that component of the propellant which boils above room temperature may be placed in the container, the valve sealed in place, and the balance of the propellant may be introduced by pressure filling through the valve nozzle. As a further alternative a bulk of the total composition may be made and portions of this bulk composition may be filled into the container through the valve. Throughout the preparation of the product care is desirably exercised to minimise the absorption of moisture. On operating the valve, the powder will be dispensed in a stream of propellant, which will vaporise providing an aerosol of powder.

The pressurised aerosol compositions of the invention may be used in the treatment of a number of allergic conditions in mammals, e.g. the inhalation treatment of reversible obstructive conditions of the airways, such as asthma or allergic rhinitis (hay fever). The treatment is preferably by oral inhalation or more preferably by nasal inhalation and is preferably treatment of man.

We also provide a composition comprising nedocromil calcium in admixture with a pharmaceutically acceptable excipient, wherein the composition may comprise less than 80% of nedocromil calcium and more preferably less than 50% w/w.

In particular, for the treatment of nasal disorders the indicated daily dosage is in the range of from 0.1 to 50 mg, preferably from 0.1 to 20 mg, more preferably from 1 to 15 mg, most preferably 2 to 11 mg and especially from 4 to 11 mg, of nedocromil calcium admixed with a solid or liquid pharmaceutically acceptable diluent, carrier or adjuvant, which may be administered in divided doses from 1 to 8 times a day, preferably from 1 to 4 times a day and more preferably twice daily or once daily.

The therapeutic activity of nasally inhaled nedocromil calcium is illustrated in standard nasal antigen challenge studies, such as those disclosed by:

(a) Guerico, J. P., et al, J Allergy Clin Immunol 1980, 66(1), 61-9, (b) Wihl, J. A., et al, Acta Otolanyngol, 1977, 84, 281-6, (c) Mygind, N., et al, Eur J Respir Dis, 1986, 68(143), 31-4, (d) Okuda, M., Arch Oto-Rhino-Laryng, 1977, 214, 241-6.

According to the invention we also provide doses and forms suitable for administration by oral inhalation comprising from 0.01 to 50 mg, preferably from 0.01 to 30 mg, more preferably from 0.01 to 20 mg, most preferably from 0.01 to 15 mg and especially from 1 to 10 mg of the compound according to the invention, preferably admixed with a solid or liquid pharmaceutically acceptable adjuvant, diluent or carrier.

For administration by oral inhalation, the new compound may be formulated with a compressed gas, e.g. nitrogen, or a liquefied propellant as a pressurised aerosol composition.

For inhalation as a powder formulation, the new compound in finely divided form may be used in admixture with a carrier of larger particle size.

According to the invention we provide nedocromil calcium in powder form for administration by inhalation in admixture with a pharmaceutically acceptable adjuvant, diluent or carrier.

Nedocromil calcium in powder form may have a water content of less than 5% w/w, preferably less than 4% w/w, more preferably less than 3% w/w and especially less than 2.5% w/w.

Alternatively, nedocromil calcium in powder form may have a water content of from 12 to 25% w/w, preferably from 15 to 25% w/w and more preferably from 15 to 20% w/w.

Powder formulations may also be prepared from nedocromil calcium having a water content different to the above.

The powder formulation may be inhaled nasally but we prefer the powder formulation to be administered by oral inhalation.

The particle size spectrum of the carrier will depend on the particular inhalation device from which the formulation is to be dispersed. It is however desirable to avoid carrier particles of less than 10 microns in size, thus minimising the number of non-drug particles which penetrate deep into the lung. A large proportion of very large particles may also cause a gritty feel in the mouth of the user and is therefore less preferred. Use of a carrier of larger particle size may also cause problems in filling when using filling machines which involve a dosator which picks up powder by dipping into a powder bed from above. However, use of a carrier of larger particle size may ease filling when using machines in which a die is filled from above, but may incline the composition to segregate during transport or storage.

The composition preferably contains from 2 to 50% by weight of the new compound, and from 50 to 98% by weight, more especially from 75 to 95% by weight and particularly from 85 to 90% by weight of the carrier.

The finely divided new compound may be prepared in the desired particle size range, for example using a ball mill, a fluid energy mill, by precipitation or by spray drying. The carrier may be prepared by spray drying or grinding and subsequently separating out the desired fraction, for example by air classification and/or sieving.

The powder compositions may be prepared by mixing the ingredients together in one or, preferably, more (e.g. two) steps in a mixer, such as a planetary or other stirred mixer.

The carrier may be any non-toxic material which is chemically inert to the new compound and is acceptable for inhalation or for administration to the nose. Examples of carriers which may be used include inorganic salts, e.g. sodium chloride or calcium carbonate; organic salts, e.g. sodium tartrate or calcium lactate; organic compounds, e.g. urea or propylidone; monosaccharides, e.g. lactose, mannitol, arabinose or dextrose monohydrate; disaccharides, e.g. maltose or sucrose, polysaccharides, e.g. starches, dextrins or dextrans. A particularly preferred carrier is lactose, e.g. crystalline lactose.

The powder compositions will generally be put up in sealed gelatine, plastic or other capsules. The container is preferably loosely filled to less than about 80% by volume, preferably less than about 50% by volume, with the powder composition. Powder formulations with a water content of less than 5% w/w are preferably put in plastic capsules, whereas powder formulations with a water content of from 12 to 25% w/w may be put in gelatin capsules.

When the new compound is to be used to treat the eye, it may be used, for example, in the form of an aqueous solution, or an aqueous suspension, or an ophthalmic ointment (e.g. in an oily base), or in a controlled release formulation, e.g. a device adapted to be inserted under the eyelid and to release the new compound at a controlled rate.

If desired, the composition may be formulated in sustained release form, e.g. by coating the drug particles with a layer of a substance which could be expected to be slowly dissolved or to act as semi-permeable membranes through which the drug can diffuse when the preparations are ingested. Specifically, there may be mentioned enteric coated formulations.

The new compound of the present invention may be used in combination with or sequentially with a wide variety of other pharmaceutically active substances. Where appropriate, the new compound may be mixed with one or more other active substances or the new compound may be chemically linked with the other active substance(s), e.g. to form a salt or ester. The particular mixture, dose regimen or chemically-linked substances used, and ratio of the active ingredients, will depend on a variety of factors including the conditions to be treated, the mode of administration, the particular active ingredients and the patient concerned.

Examples of compounds with which the present compound may be mixed or chemically linked include beta-stimulant bronchodilators, for example, fenoterol, reproterol, pirbuterol, rimiterol, orciprenaline, terbutaline or salbutamol;

steroids such as hydrocortisone, and more active compounds such as betamethasone valerate, clobetasone butyrate, fluocinolne acetonide, fluocortolone hexanoate, beclamethasone dipropionate, hydrocortisone butyrate, diflucortolone valerate, triamcinolone acetonide, fluocinonide, desonide, flurandrenalone, flumethasone pivalate, methylprednisolone, clobetasol propionate, halcinonide, tixocortol, prednisolone and flupredynlidene-21-acetate.

The new compound of the invention may be used in a variety of dosing schedules, either on its own or in conjunction with one or more of the other active ingredients listed herein. The priming dose may be substantially smaller or substantially larger than the maintenance dose. The new compound, when used in conjunction with another active ingredient, may be used together with, before or after the other active ingredient depending on the desired combined effect of the compounds. The different active ingredients may be administered by the same or different routes.

The invention is illustrated, but in no way limited, by the following Examples.

EXAMPLE 1

Calcium 9-ethyl-6,9-dihydro-4,6-dioxo-10-propyl-4H-pyrano-[3,2-g]-quinoline-2,8-dicarboxylate A filtered solution of disodium 9-ethyl-6,9-dihydro-4,6-dioxo-10-propyl-4H-pyrano-[3,2-g]-quinoline-2,8-dicarboxylate (75 g) in water (500 ml) was treated with a filtered solution of calcium nitrate (77 g) in water (500 ml). The mixture was stirred (2 hours) and then filtered. The solid obtained was washed with water and acetone, slurried first with water and then reslurried with acetone (500 ml). The solid was filtered off and dried in vacuo at 65° C. to give the title compound (73 g, contains 19.3% w/w water).

$C_{19}H_{15}NO_7Ca$: Requires: C, 55.74; H, 3.69; N, 3.42; Ca, 9.79%. Requires: C, 44.98; H, 2.96; N, 2.75; Ca, 7.89%. (for 19.3% water) Found: C, 44.58; H, 3.09; N, 2.76; Ca, 7.78%.

EXAMPLE 2

Calcium 9-ethyl-6,9-dihydro-4,6-dioxo-10-propyl-4H pyrano[3,2-g]quinoline-2,8-dicarboxylate A filtered solution of disodium 9-ethyl-6,9-dihydro-4,6-dioxo-10-propyl-4H-pyrano[3,2-g]quinoline-2,8dicarboxylate (500 g) in 3.4 liters of water was treated with a filtered solution of calcium nitrate tetrahydrate (513 g) in 3.4 liters of acetone. The mixture was stirred slowly for 2 hours at ambient temperature and the precipitate then filtered off and washed with water and acetone. The solid was then slurried in 3 liters of water and filtered; this was followed by a slurry in 3-4 liters of acetone and refiltration.

The damp solid was dried, in vacuo, at 65° C. to give 547 g of the title compound (contains 10.9% w/w water).

$C_{19}H_{15}NO_7Ca$: Requires: C, 55.74; H, 3.69; N, 3.42; Ca, 9.79%. Requires: C, 49.65; H, 4.50; N, 3.05; Ca, 8.72%. (for 10.9% water) Found: C, 49.65; H, 4.51; N, 3.17, Ca, 7.93%.

EXAMPLE 3

Calcium 9-ethyl-6,9-dihydro-4,6-dioxo-10-propyl-4H-pyrano[3,2-g]quinoline-2,8-dicarboxylate 9-Ethyl-6,9-dihydro-4,6-dioxo-10-propyl-4H-pyrano[3,2-g]quinoline-2,8-dicarboxylic acid (5 g) was suspended in water (125 ml) and was treated with calcium nitrate (5.1 g) in water (35 ml). The mixture was stirred at room temperature for two hours and the precipitate was filtered off and washed with water and acetone.

The damp solid was dried in vacuo at 65° C. to give 4.8g of the title compound (contains 18.8% w/w water). $C_{19}H_{15}NO_7Ca$: Requires: C, 55.74; H, 3.69; N, 3.42; Ca, 9.79%. Requires: C, 50.83; H, 2.49; N, 2.31; Ca, 6.62%. (for 18.8% water) Found: C, 50.61; H, 2.45; N, 2.90, Ca, 6.08%.

EXAMPLE 4

(a) Administration of intranasal suspension

The administration of nedocromil calcium was investigated in healthy volunteers.

A 2% w/v and 4% w/v aqueous suspension of nedocromil calcium was administered using a standard nasal pump in 0.25 ml doses (0.125 ml per nostril), corresponding to doses of 5 and 10 mg respectively.

1%, 2 % and 4 % w/v aqueous solutions of nedocromil sodium were administered for comparison.

The incidence of the feeling of warmth as a side effect was markedly reduced with the nedocromil calcium in comparison with the nedocromil sodium.

(b) Administration of intranasal pressurised aerosol

The administration of nedocromil calcium was investigated in healthy volunteers.

Nedocromil calcium was administered using a pressurised aerosol delivering a dosage of 2.6 mg of nedocromil calcium per actuation. A total dosage of 5.2 mg of nedocromil calcium was administered.

A 1% w/v aqueous solution of nedocromil sodium was administered for comparison.

Plasma and urine samples were analysed for nedocromil calcium and nedocromil sodium content using radioimmunoassay.

Nedocromil calcium produced lower peak plasma levels, sustained plasma concentrations and slower clearance from the nasal cavity over nedocromil sodium.

EXAMPLE 5

Oral Administration 100 mg doses of nedocromil calcium were administered orally three times daily for seven days to 10 healthy volunteers.

Symptoms experienced by the volunteers during this period were recorded.

Five out of the ten volunteers recorded no symptoms throughout the seven day treatment period.

These results were compared to a similar study undertaken using nedocromil sodium in which ten volunteers received 100 mg nedocromil sodium orally three times a day for four days. Seven of the volunteers reported gastro-intestinal disturbances.

EXAMPLE 6

The activity of nedocromil calcium has been evaluated by the antigen inhalation test on human volunteers who suffer from specific allergic asthma. The degree of asthma provoked by the inhalation of an antigen to which the volunteers are sensitive can be measured by repeated estimation of the increase of airway resistance.

A suitably designed spirometer was used to measure the forced expiratory volume at one second (FEV1) and hence the changes in the airway resistance. The anti-allergic activity of nedocromil calcium is estimated from the difference between the maximum per cent $FEV_1$ reduction following control and test provocations after drug administration conducted under identical experimental conditions.

Thus:

$$\% \text{ protection} = 100 \times \frac{Av \max \% FEV_1 \text{ fall control shock} - \max \% FEV\ 1.0 \text{ fall test shock}}{Av \max \% FEV_{1.0} \text{ fall control shock}}$$

Nedocromil calcium was administered by inhalation at the desired time before challenge with antigen.

Example 7

| (i) Pressurised Aerosol Formulations for nasal administration | | | |
|---|---|---|---|
| | | | % w/w |
| (a) | Nedocromil calcium (micronised) | | 4.0 |
| | Sorbitan trioleate | | 0.5 |
| | 1,2-Dichlorotetrafluorethane BP | | 38.2 |
| | Dichlorodifluoromethane BP | | 57.3 |
| (b) | Nedocromil calcium (micronised) | | 3.9 |

| -continued | |
|---|---|
| Docusate calcium BP | 0.5 |
| 1,2-Dichlorotetrafluorethane BP | 76.5 |
| Dichlorofluoromethane BP | 19.1 |

| (ii) Dry Powder Formulation for oral inhalation | |
|---|---|
| | Percentage by weight |
| Nedocromil calcium | 1.43 |
| Lactose | 98.57 |

The skilled man will, of course, be able to vary these quantities according to the form of nedocromil calcium used.

What we claim is:

1. Calcium 9-ethyl-6,9-dihydro-4,6-dioxo-10-propyl-4H-pyrano[3,2-g]-quinoline-2,8-dicarboxylate.

2. The compound according to claim 1, wherein the water content is from 12 to 25% w/w.

3. A method of treatment of reversible obstructive airways disease which comprises administering a therapeutically effective amount of nedocromil calcium to a patient suffering from such a condition.

4. A method of treatment of rhinitis which comprises administering a therapeutically effective amount of nedocromil calcium to a patient suffering from such a condition.

5. A composition for treatment of reversible obstructive airways disease comprising an effective proportion of a compound according to claim 1 in admixture with a pharmaceutically acceptable adjuvant, diluent, or carrier.

6. A composition in accordance with claim 5 in powder form for administration by inhalation.

7. A composition in accordance with claim 6 in a pressurized aerosol formulation in admixture with a liquefied propellant.

8. A composition in accordance with claim 7 wherein said compound of claim 1 has a water content of less than 5% w/w.

9. A method for treating reversible obstructive airways disease or rhinitis comprising administering an effective amount of the compound of claim 1 to a patient suffering or likely to be suffering from such a condition.

* * * * *